(12) United States Patent
Lin

(10) Patent No.: US 6,325,827 B1
(45) Date of Patent: Dec. 4, 2001

(54) INTERVERTEBRAL IMPLANT

(75) Inventor: Paul S. Lin, Lewisburg, PA (US)

(73) Assignee: BlackSheep Technologies, Inc., Lewisburg, PA (US)

( * ) Notice: Subject to any disclaimer, the term of this patent is extended or adjusted under 35 U.S.C. 154(b) by 0 days.

(21) Appl. No.: 09/288,651

(22) Filed: Apr. 9, 1999

Related U.S. Application Data

(60) Provisional application No. 60/118,115, filed on Feb. 1, 1999.

(51) Int. Cl.$^7$ ........................................... A61F 2/44
(52) U.S. Cl. ........................................... 623/17.16
(58) Field of Search .................. 623/11, 17, 11.11, 623/17.11, 17.15, 17.16, 16.11; 606/53, 60, 61

(56) References Cited

U.S. PATENT DOCUMENTS

| | | |
|---|---|---|
| 4,349,921 * | 9/1982 | Kuntz ........................ 623/17 |
| 4,772,287 | 9/1988 | Ray et al. . |
| 4,820,305 | 4/1989 | Harms et al. . |
| 4,834,757 * | 5/1989 | Brantigan ..................... 623/17 |
| 4,878,915 | 11/1989 | Brantigan . |
| 4,898,161 | 2/1990 | Grundel . |
| 4,936,848 | 6/1990 | Bagby . |
| 4,961,740 | 10/1990 | Ray et al. . |
| 5,015,247 | 5/1991 | Michelson . |
| 5,015,255 | 5/1991 | Kuslich . |
| 5,026,373 | 6/1991 | Ray et al. . |
| 5,055,104 | 10/1991 | Ray et al. . |
| 5,059,193 | 10/1991 | Kuslich . |
| 5,147,402 | 9/1992 | Bohler . |
| 5,263,953 | 11/1993 | Bagby . |
| 5,306,307 * | 4/1994 | Senter et al. ................... 623/17 |
| 5,339,194 | 8/1994 | Mikhail . |
| 5,423,817 | 6/1995 | Lin . |
| 5,425,772 | 6/1995 | Brantigan . |
| 5,489,307 | 2/1996 | Kuslich et al. . |
| 5,489,308 | 2/1996 | Kuslich et al. . |
| 5,505,732 | 4/1996 | Michelson . |
| 5,514,180 | 5/1996 | Heggeness et al. . |
| 5,562,662 | 10/1996 | Brumfield et al. . |
| 5,607,424 * | 3/1997 | Tropiano ........................ 606/61 |
| 5,609,635 | 3/1997 | Michelson . |
| 5,630,816 | 5/1997 | Kambin . |
| 5,653,761 | 8/1997 | Pisharodi . |
| 5,653,762 | 8/1997 | Pisharodi . |
| 5,658,336 * | 8/1997 | Pisharodi ..................... 623/17 |
| 5,658,356 | 8/1997 | Pishanodi . |
| 5,665,122 | 9/1997 | Kambin . |

(List continued on next page.)

OTHER PUBLICATIONS

Depraetere et al., Interbody Cages in PLIF Surgery, A Multicentric Report.
Brantigan, I/F Cage for PILF, Acromed.
BAK/Proximity Posterior Interbody Fusion System, Spin-etech.
Ray et al., A Prosthetic Lumbar Nucleus Artificial Disc, Stryker Implants.
A Cellular Structural Biomaterial, Hedrocel.

*Primary Examiner*—Eduardo C. Robert
(74) *Attorney, Agent, or Firm*—Calfee, Halter & Griswold, LLP

(57) ABSTRACT

An intervertebral implant has an elongated body that is narrower on each end than in the middle thereof. The body includes interconnected, parallel walls that include barbs positioned along the outer edges thereof. The barbs are typically inclined rearwardly thereby allowing easy insertion, yet preventing retropulsion or migration of the implant from the vertebral interspace. A distraction tool includes a distal end having a cross section that has two diagonally opposed rounded corners and two diagonally opposed square corners. An intervertebral implant instrumentation kit for surgically inserting an intervertebral implant into the interspace between adjacent vertebrae includes a distraction tool and the intervertebral implant.

16 Claims, 5 Drawing Sheets

U.S. PATENT DOCUMENTS

| | | |
|---|---|---|
| 5,683,391 * | 11/1997 | Boyd ........................................ 606/61 |
| 5,693,100 | 12/1997 | Pisharodi . |
| 5,709,683 | 1/1998 | Bagby . |
| 5,716,355 | 2/1998 | Jackson et al. . |
| 5,720,748 | 2/1998 | Kuslich et al. . |
| 5,766,252 | 6/1998 | Henry et al. . |
| 5,776,199 | 7/1998 | Michelson . |
| 5,785,710 * | 7/1998 | Michelson ................................ 623/17 |
| 5,797,917 | 8/1998 | Boyd et al. . |
| 5,803,904 | 9/1998 | Mehdizadeh . |
| 5,860,977 | 1/1999 | Zucherman et al. . |
| 5,865,845 | 2/1999 | Thalgott . |
| 5,865,847 | 2/1999 | Kohrs et al. . |

* cited by examiner

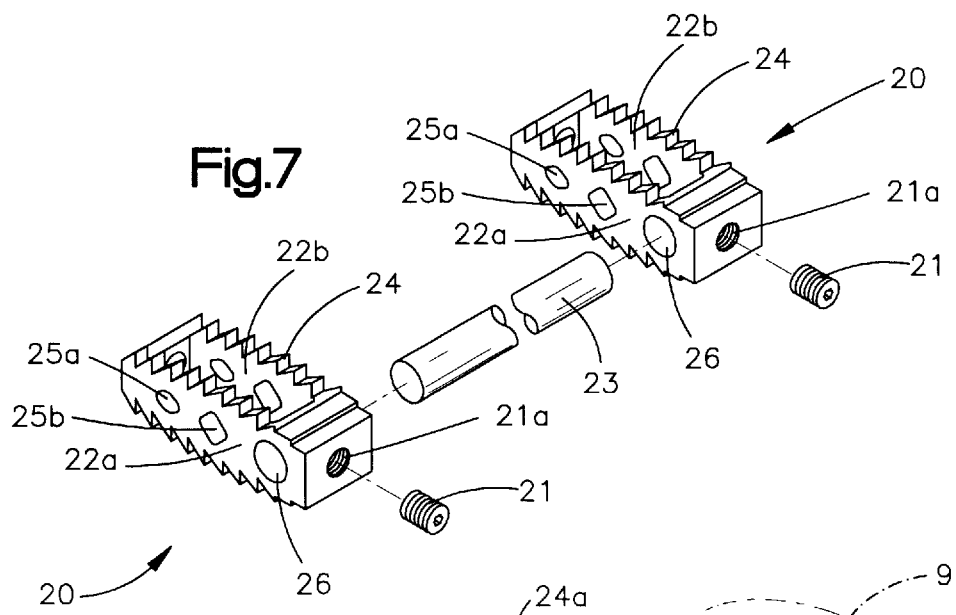
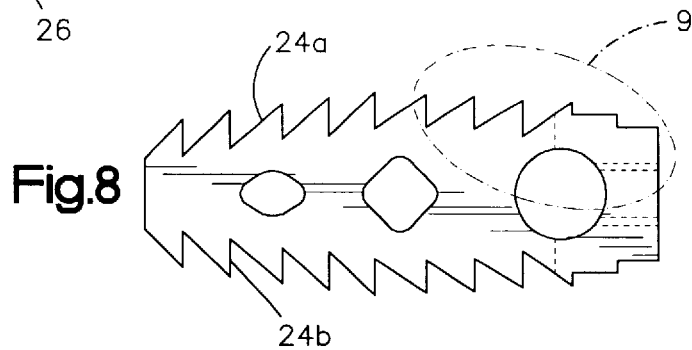
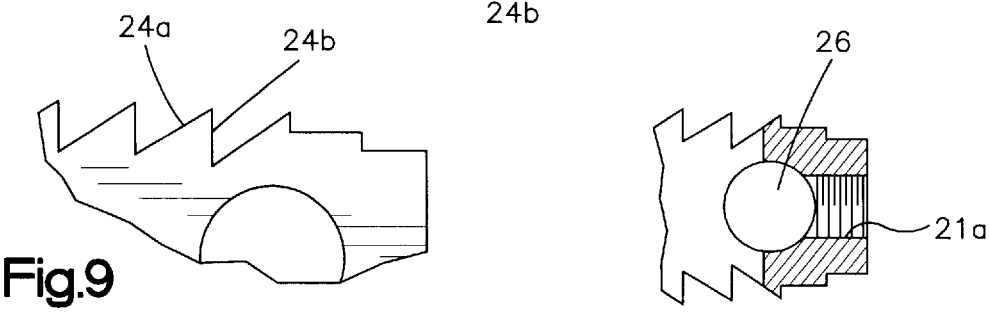
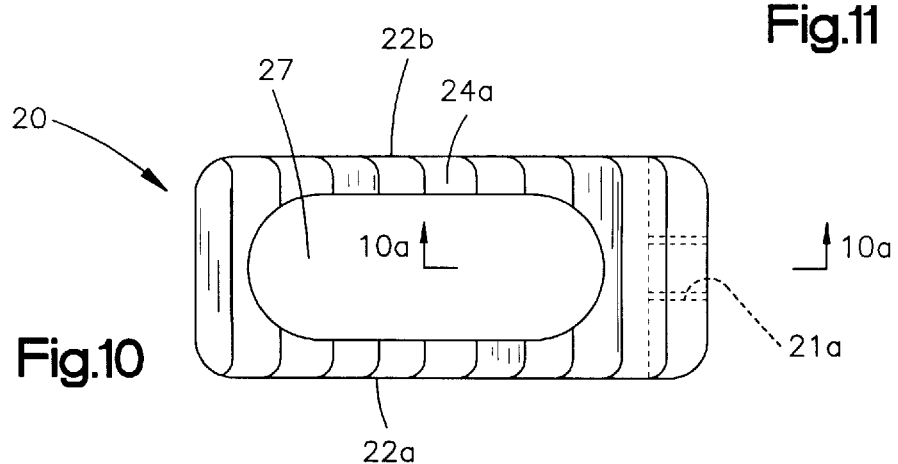

INTERVERTEBRAL IMPLANT

CROSS REFERENCE TO RELATED APPLICATION

This application claims the priority of Provisional Patent Application No. 60/118,115, filed on Feb. 1, 1999.

BACKGROUND OF THE INVENTION

The field of this invention is intervertebral implant instrumentation and methods of implantation.

A variety of different intervertebral implants and distraction tools have been designed, used and patented. Intervertebral implants are used to replace diseased or damaged vertebral discs. Some implant designs are hollow to allow for the insertion of bone graft material that can fuse adjoining vertebrae. Some implant designs are nearly square in shape. The square shape typically tends to prevent the easy insertion of the implant into the intervertebral space. Many of the existing implant designs require complex and potentially dangerous pre-drilling and tapping of the intervertebral space prior to inserting the implant.

Some implants include vertical ridges at the surfaces that contact the vertebral laminar surface. Simple vertical ridges typically do not prevent retropulsion of the implant relative to the intervertebral space. Furthermore, vertical ridges can prevent easy insertion of the implant.

In some instances, the surgical implant can become unstable after the surgical insertion. The implant can be subject to torsional forces that can jeopardize the integrity of the procedure.

A distraction tool is used for preparing an intervertebral space prior to insertion of an implant. Some of the existing distraction tools include a tapered proximal end and some include square corners about the cross section. The square cross section provides a stable footing once the distractor is inserted. Other distraction tools include rounded corners about the cross section. Such a configuration allows for easy insertion of the distractor.

SUMMARY OF THE INVENTION

This invention relates to new and improved intervertebral implant instrumentation and methods of intervertebral implantation. According to the invention, an intervertebral implant is provided that has an elongated body that is narrower on each end than in the middle. The body includes interconnected, parallel walls that include barbs positioned along the outer edges thereof. The barbs are typically inclined rearwardly thereby allowing easy insertion, yet preventing retropulsion or migration of the implant from the vertebral interspace.

In another aspect, the invention relates to an intervertebral implant distraction tool that includes a body that has an ellipsoidal shaped end, a shank that is narrower than the ellipsoidal shaped end and a handle. The Ellipsoidal shaped end has a cross section that comprises a rounded edge on each of two diagonally opposed corners and a square edge on each of two diagonally opposed corners. The unique corner configuration of the distraction tool allows easy insertion between adjacent vertebrae and provides a stable footing once the distractor is inserted.

An inventive intervertebral implantation kit for surgically inserting an intervertebral implant into an interspace between adjacent vertebrae comprises the intervertebral implant and a distraction tool.

BRIEF DESCRIPTION OF THE DRAWINGS

These features and advantages of the invention may be more clearly understood by referring to the drawings where like elements correspond to like numbers and wherein:

FIG. 7 is an exploded, perspective view of two, rod-type interconnecting intervertebral implants and the inventive rod cross-link assembly;

FIG. 8 is a side view of the rod-type, interconnecting implant embodiment;

FIG. 9 is an expanded detail view of the barbs taken from FIG. 8;

FIG. 10 is a top view of the implant shown in FIG. 8;

FIG. 11 is a sectional view of section 10a from the implant embodiment shown in FIG. 10;

DETAILED DESCRIPTION

Figure 1:
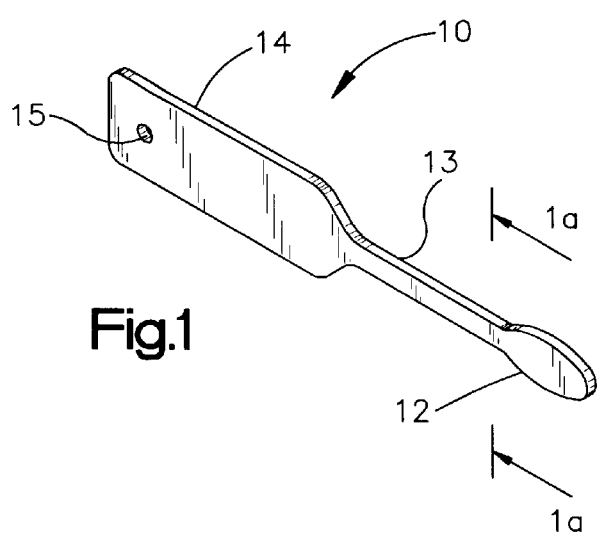
FIG. 1 is a perspective view of the distraction tool.

A lateral x-ray of a lumbar interspace shows that surfaces to the bony endplate are not planer but rather are curved. The intervertebral implant of the invention advantageously mirrors these curved surfaces. The implant has two connected, substantially parallel walls that are narrower at the ends than the center. The walls define an elongate spacer body with oblate spheroid profile. The spheroid body profile is arched with truncated ends. The body includes at least two opposing rows of biased metallic, angled barbs. The barbs can be positioned along the top and bottom edges of the implant walls. An important feature of the barbs is the configuration of the barb faces. The front face of the barbs is angled rearwardly relative to the direction of insertion of the implant. The rear face is angled approximately vertical. The rear face may also be angled rearwardly relative to the direction of insertion of the implant. The rearward angular orientation of the barbs allows the implant to be easily inserted either posteriorly or anteriorly. Once inserted, the angular orientation resists retropulsion and implant migration.

To insert the implant, a distraction force can be applied to open the interspace. The implant is then placed within and hammered into a tight fit. Advantageously, the implant (1) is easily inserted by means of standard instrumentation, (2) preserves the endplate and (3) provides a secure tension fit within the interspace. Insertion of the implant does not require interspace preparation with reamers and taps.

The walls of the implant can have openings therein so that bone graft material can be inserted to provide fusion between adjacent vertebrae and the implant body. Alternatively, the bone graft material can be contained within a polymer type bag member. The bag member is inserted into the body between the parallel walls. The bag can contain a bone morphogenic substance that leaches out of the bag member to allow fusion of adjacent vertebral bodies.

An interconnecter can be provided to connect multiple implants together. The interconnecter can include an elongated member having a channel along a portion of each end. Each body to be interconnected includes a slot on the end of the body that corresponds to the width of the elongated member. A connector such as a pin, rivet or threaded screw can be used to securely fasten the elongated member to each end of the implant bodies.

An alternative interconnecter is also provided that includes an elongated member that is adjustably positioned within openings contained in the implant bodies. The elongated member is adjustably secured to the implant bodies with a securing member such as a pin, rivet or threaded screw member.

The interconnecter provides unique torsional stability to the intervertebral implant construct. The connection provided with the interconnecter is somewhat similar to diagonal 2×4 bracing that is used together with vertical 2×4 members in building construction. These and other features will become apparent from the drawings and the detailed discussion that follows, which by way of example without limitation, describe preferred embodiments of the present invention. The following table includes the descriptions of the parts and their corresponding reference numbers as provided in the drawings and described herein:

| Reference Number: | Description: |
|---|---|
| 10 | Distraction Tool |
| 12 | Distal End of Distraction Tool |
| 13 | Neck |
| 14 | Handle |
| 15 | Hole |
| 16a, 16b | Rounded Corners of Distraction Tool |
| 18a, 18b | Square Corners of Distraction Tool |
| 19a, 19b | Upper and Lower Ends of Distal End of Distraction Tool |
| L2, L3, L4 | Lumbar Vertebrae |
| 20 | Rod-type Interconnecting Implant |
| 21 | Machine Screw |
| 21a | Threaded Bore |
| 22a, 22b | Walls |
| 23 | Rod |

-continued

| Reference Number: | Description: |
|---|---|
| 24 | Barb |
| 24a | Front Face of Barb |
| 24b | Rear Face of Barb |
| 25a | Front Wall Opening |
| 25b | Center Wall Opening |
| 26 | Rod Bore |
| 27 | Top Opening |
| 30 | Plate-type Interconnecting Implant |
| 31 | Connecting Pin |
| 31a | Pin Head |
| 31b | Pin Shaft |
| 31c | Pin Bore |
| 32a, 32b | Walls |
| 33 | Cross-link Plate |
| 33a | Slot |
| 33b | Channel |
| 34 | Barb |
| 34a | Front Face of Barb |
| 34b | Rear Face of Barb |
| 35a | Front Wall Opening |
| 35b | Center Wall Opening |
| 35c | Rear Wall Opening |
| 36 | Groove |
| 36a, 36b | Groove Side Walls |
| 37 | Top Opening |

Intervertebral Implant Instrumentation Kit

In a preferred embodiment of the present invention, a distraction tool 10, rod-type intervertebral implant 20 and plate-type intervertebral implant 30 are provided.

The distraction tool 10 is illustrated in FIGS. 1, 1a, 2a, 2b, 3a and 3b. The distraction tool 10 includes a tapered distal end 12. The tapered end 12 allows for easy insertion of the distraction tool 10 and helps to prevent damage to the intracanal neural structures during the distraction procedure. There is a relatively narrow neck 13 that connects the distal end 12 to the handle 14. A hole 15 can be provided in the handle 14 for insertion of a leverage bar.

Figure 1A:
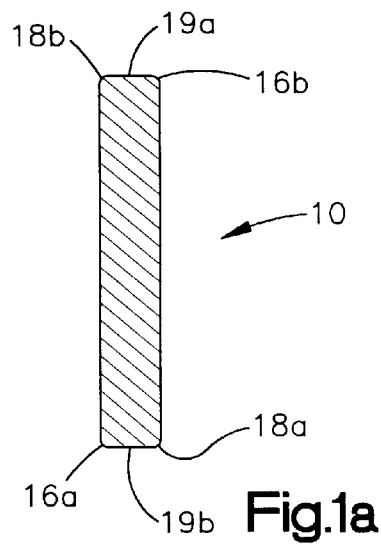
FIG. 1a is a sectional view of section 1a of the proximal end of the distraction tool.

The cross section taken from across section 1a of the distal end of the distraction tool 10 in FIG. 1 is illustrated in FIG. 1a. The cross section shows the important corner feature of the distraction tool 10. Diagonally opposed corners 16a, 16b are rounded while diagonally opposed corners 18a, 18b are square. The diagonally opposed rounded corners 16a, 16b permit the spinal surgeon to easily rotate the distal end of the distraction tool 10 within the intervertebral interspace. The square corners 18a, 18b provide the advantage of establishing a stable footing between upper and lower ends 19a, 19b of the distal end 12 of the distraction tool 10 relative to the inner cortices of the adjacent vertebrae.

The intervertebral distraction tool 10 can comprise any biocompatible material, preferably titanium or stainless steel.

The instant distraction tool 10 may be used with any desired intervertebral implant. The distraction tool's use and advantages are not limited to the inventive implants described herein.

Figure 4:
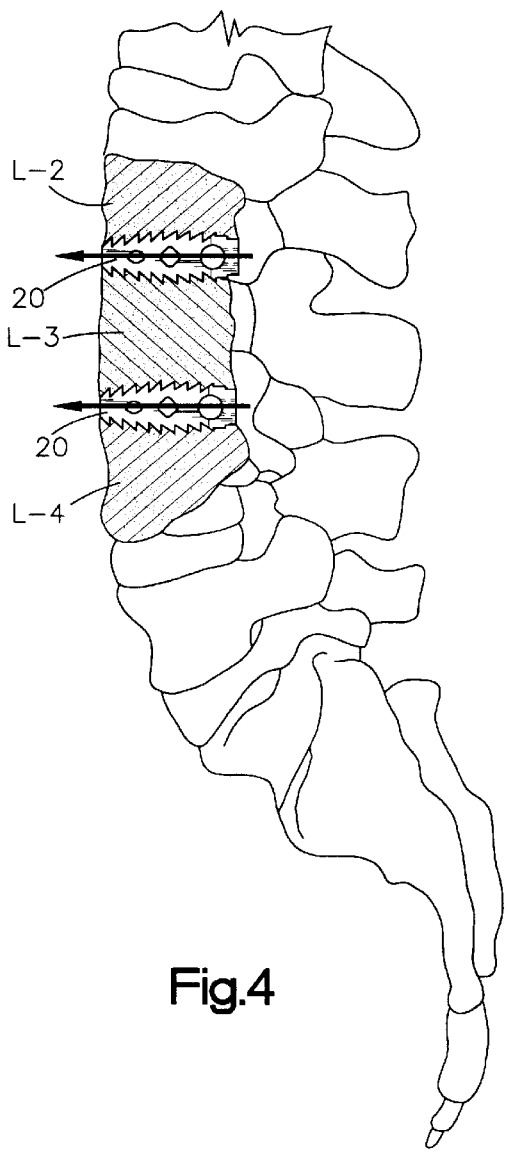
FIG. 4 is a lateral view of the lumbar region of the spinal column showing two, rod-type interconnecting intervertebral implants therein.

The rod-type intervertebral implant 20 is shown installed between the L-2 and L-3 lumbar vertebrae and between the L-3 and L-4 vertebrae in FIG. 4. Two of the rod-type implants 20 are also shown installed in the interspace between the L-2 and L-3 vertebrae in FIG. 5. Detailed views of the rod-type implant are shown in FIGS. 7, 8, 9, 10 and 11.

The rod-type intervertebral implant 20 includes a body having two connected, substantially parallel walls 22a, 22b.

Each end of the walls 22a, 22b is narrower than the width at the center thereof. The walls define an elongate spacer body with oblate spheroid profile. The spheroid body profile is arched with truncated ends as shown. The body includes at least two opposing rows of biased metallic, angled barbs. As shown, barbs 24 can be positioned along the top and bottom edges of the walls 22a, 22b. An important feature of the barbs 24 is the configuration of the barb faces. The front face 24a of the barbs 24 is angled rearwardly relative to the direction of insertion of the implant 20. The rear face 24b of the barbs 24 is angled approximately vertical. The rear face may also be angled rearwardly relative to the direction of insertion of the implant 20. The rearward angular orientation of the barbs allows easy insertion of the implant 20. After insertion, the barbs resist implant retropulsion and migration.

Figure 5:
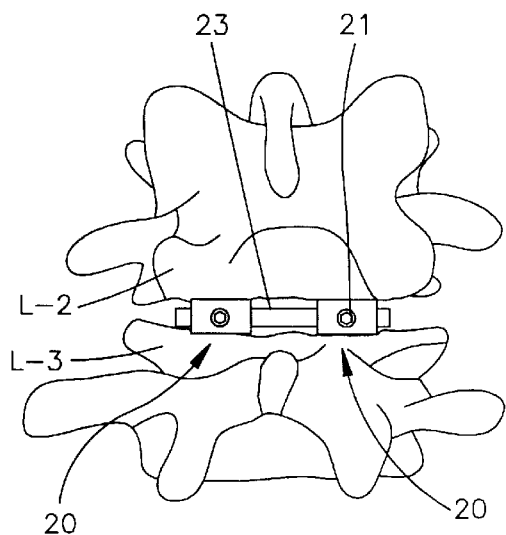
FIG. 5 is a dorsal view of two intervertebral implants interconnected with the inventive rod-type cross-link assembly.

The rod-type implant 20 includes a rod bore 26 that is sized to receive the rod 23. After the rod-type implants 20 are installed as shown in FIG. 5, the rod 23 can be inserted through each of the rod bores 26 in each implant 20. The rod 23 is secured to the implant 20 with a machine screw 21 on each implant 20. Each machine screw 21 is threaded into the corresponding threaded bore 21a. Alternative securing means may also be used. The interconnection provided between the implants 20 creates important torsional stability between the implants 20. The implants 20 will not always need to be interconnected with the rod 23. However, if desired or required, the interconnection will provide the surgeon and the patient with a superior, stable construct.

It is contemplated that other longitudinal members can be used instead of the round cross section configuration of the rod 23. For example, the rod can be square, oval, triangular, hexagonal or other geometric configurations in cross section.

The body of the rod-type implant 20 includes a hollow opening 27 to allow for filling with bone graft. Openings 25a, 25b are also provided in the walls 22a, 22b. The openings 22a, 22b allow bone graft material to extend beyond the inside of the implant body to form a more complete fusion of the implant 20 with adjacent vertebrae.

Although not shown, a bag member can be used as a carrier of the bone graft material. The bag may be inserted within space 27 of the rod-type implant 20. The bag may be constructed of a polymer or other biocompatible material. The bone material can include a morphogenic protein.

The plate-type intervertebral implant 30 includes a body having two connected, substantially parallel walls 32a, 32b. Each end of the walls 32a, 32b is narrower than the width at the center thereof. Barbs 34 are positioned along the top and bottom edges of the walls 32a, 32b. As with the rod-type implant 20, an important feature of the barbs 34 is the configuration of the barb faces. The front face 34a of the barbs 34 is angled rearwardly relative to the direction of insertion of the implant 30. The rear face 34b of the barbs 34 is angled approximately vertical. The rear face 34b may also be angled rearwardly relative to the direction of insertion of the implant 30. The rearward angular orientation of the barbs provides substantial advantages. The orientation allows easy insertion of implant 30 but resists retropulsion or the backing out of the implant 30.

Figure 6:
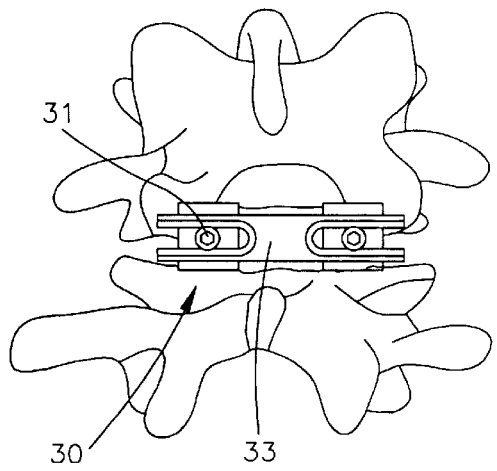
FIG. 6 is a dorsal view of two intervertebral implants interconnected with the inventive plate-type cross-link assembly.
Figure 12:
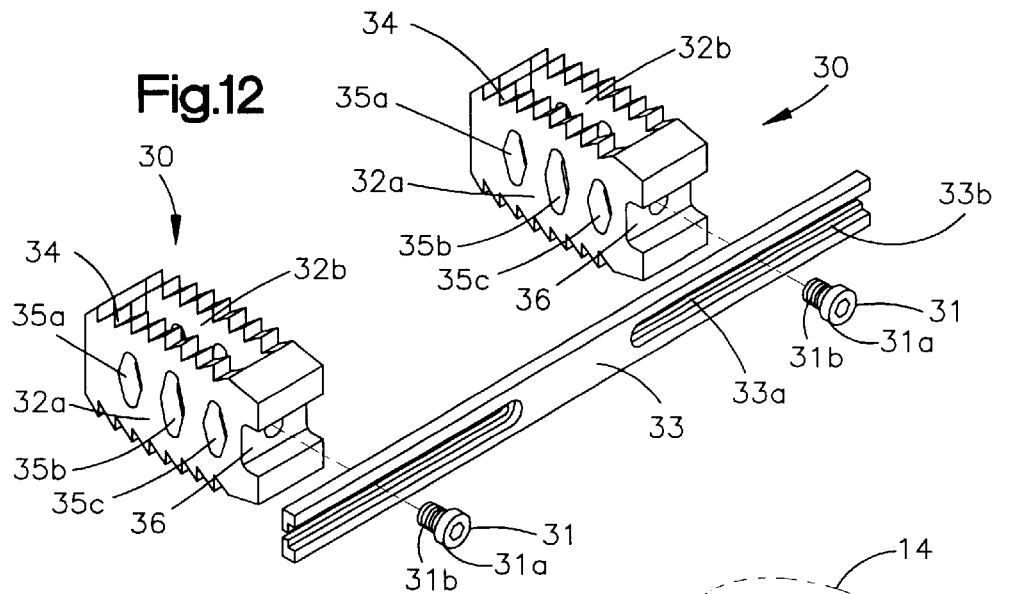
FIG. 12 is an exploded, perspective view of two, plate-type, interconnecting intervertebral implants and the inventive plate cross-link assembly.
Figure 13:
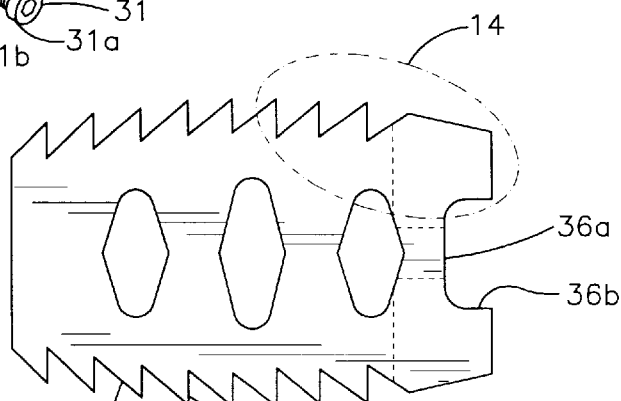
FIG. 13 is a side view of the plate-type, interconnecting implant embodiment.
Figure 14:
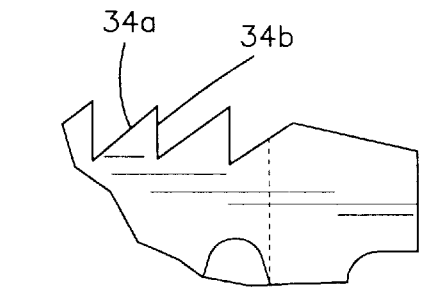
FIG. 14 is an expanded detail view of the barbs taken from FIG. 13.
Figure 16:
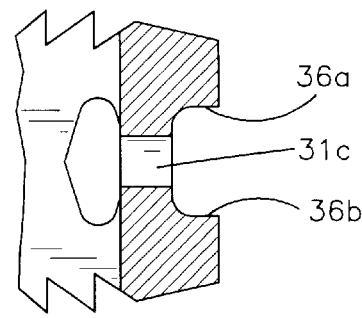
FIG. 16 is a sectional view of section 15a from the implant embodiment shown in FIG. 15.
Figure 15:
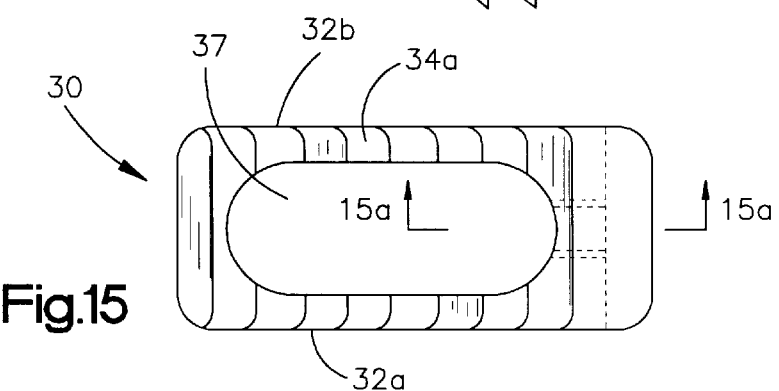
FIG. 15 is a top view of the implant shown in FIG. 13.
Figure 17:
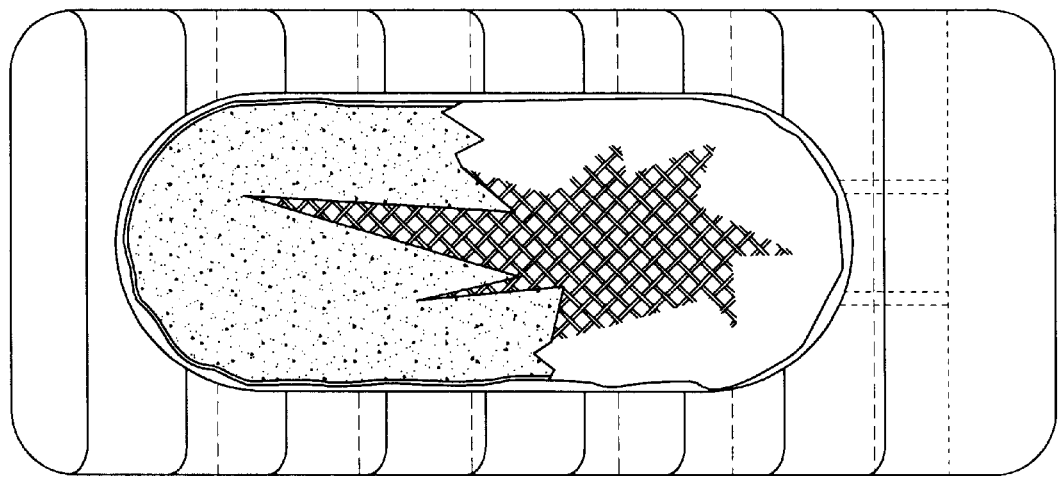
FIG. 17 is a top view of the implant containing bone material within a bag member.
Figure 18:
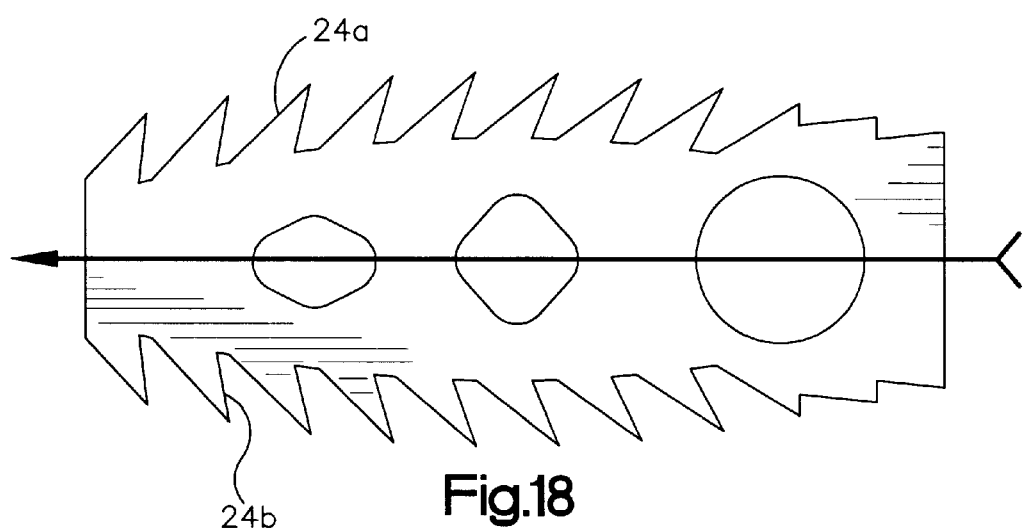
FIG. 18 is a side view of an implant showing an alternative embodiment of the barbs.

The plate-type implant 30 includes a slot 36 that is sized to receive a cross-link plate 33. The distance between the groove side walls 36a, 36b corresponds to the outer width of the cross-link plate 33. After the plate-type implants 30 are installed as shown in FIG. 6, the cross-link plate 33 can be inserted into the grooves 36 in each implant 30. The plate 33 is secured to the implant 30 with a connecting pin 31 on each implant 30. The connecting pin 31 includes a pin head 31a that is sized to fit within the channel 33b such that the underside of the pin head 31a contacts the top of the channel 33b. The connecting pin shaft 31b is sized to slide within slot 33b. The connecting pin is force fit into the pin bore 31c. Alternative securing means such as a rivet or threaded screw may also be used. As with the rod-type implant 20, the interconnection provided between the implants 30 creates important torsional stability between the implants 20. The implants 20 will not always need to be interconnected with the rod 23. However, if desired or required, the interconnection will provide the surgeon and the patient with a superior, stable construct.

The body of the plate-type implant 30 includes a hollow opening 37 to allow for filling with bone graft. Openings 35a, 35b, 35c are also provided in the walls 32a, 32b. The openings 35a, 35b, 35c allow bone graft material to extend beyond the inside of the implant body to form a more complete fusion of the implant 30 with the existing anulus fibrosus and adjacent vertebrae.

Although not shown, a bag member may also be used a carrier of the bone graft material. The bag may be inserted within space 37 of the plate-type implant 30. The bag may be constructed of a polymer or other biocompatible material. The bone material can include a morphogenic protein.

A preferred construction material for the intervertebral implant of the invention is titanium or titanium alloy but any desired biocompatible material may be used. Alternative examples of construction material include stainless steel, carbon fiber and medical grade polymer. Titanium is preferred because it can be sharpened to a point to provide barbs 34 with improved resistance to retropulsion.

Either of the intervertebral implants 20, 30 may be sized according to the corresponding vertebral interspace in which the implant will be installed.

Method of Intervertebral Disc Implantation

Figure 2A:
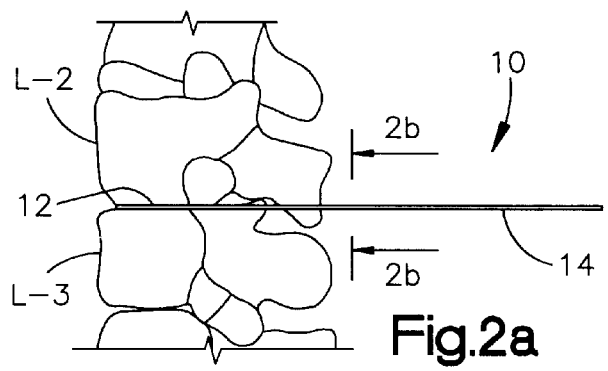
FIG. 2a is a lateral view of the edge of the distraction tool after insertion of the distraction tool after insertion into the interspace between adjacent vertebrae.
Figure 2B:
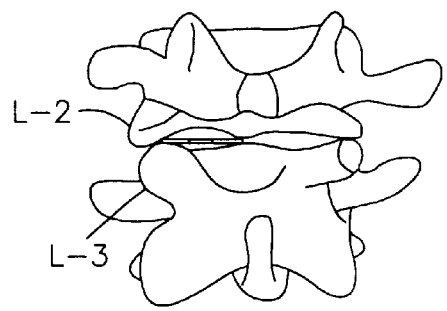
FIG. 2b is a sectional end view of section 2b of the distraction tool after insertion into the interspace between adjacent vertebrae.
Figure 3A:
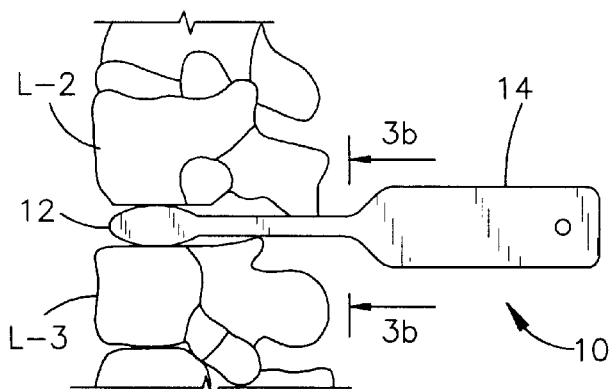
FIG. 3a is a lateral side view of the distraction tool after rotation of the tool within the interspace between adjacent vertebrae.
Figure 3B:
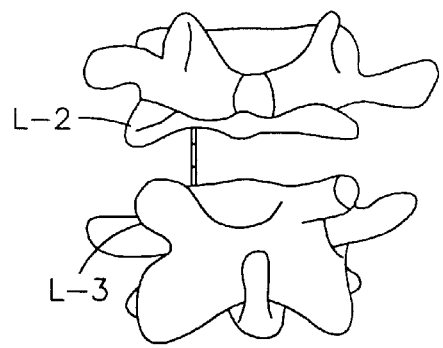
FIG. 3b is a sectional end view of section 3b of the distraction tool after rotation of the tool within the interspace between adjacent vertebrae.

In a preferred surgical method according to the present invention, the distal end 12 of the distraction tool 10 is inserted bilaterally between two adjacent vertebrae as illustrated in FIG. 2a, 2b. Although the lumbar vertebrae L-2 and L-3 are illustrated in the figures, the present method may be used for distraction between any two desired adjacent vertebrae. Although the method is illustrated posteriorly, it is contemplated that the method may also be performed anteriorly. The distraction tool is rotated clockwise so that the rounded corners 16a, 16b contact the inner cortices of the adjacent vertebrae L-2, L-3. Clockwise rotation continues until the desired opening is created within the vertebral interspace as illustrated in FIGS. 3a, 3b.

Once the required opening is formed, the desired intervertebral implant is inserted in the intervertebral interspace. The inventive intervertebral implants 20, 30 may be used as described herein or alternative implants may be used. The distraction tool 10 can then easily be removed by rotating the tool in a counter-clockwise direction and withdrawing the distraction tool 10. The rounded diagonally opposed corners 19a, 19b can also be reversed in orientation if desired whereby the rounded corners are on the upper left and lower right corners of the sectional view shown in FIG. 1a. Similarly, the diagonally opposed square corners 18a, 18b can be reversed in orientation whereby the square corners are on the upper right and lower left of the sectional view shown in FIG. 1a. If such a reversal of orientations is provided, the direction of rotation of the distraction tool 10 will be reversed such that during insertion the tool is rotated counter-clockwise and during withdrawal it is rotated clockwise.

EXAMPLES

A study was conducted with intervertebral implants having oblate spheroid profile and inclined barbs. The study included (1) eleven cases of severe stenosis or spondylolisthesis treated with complete dorsal decompression and/or reduction of spondylolisthesis with insertion of posteriorly placed intervertebral implants with screw plate fixation, (2) seven cases of posteriorly inserted implants with preservation of the facet joints and Songer cable spinous process fixation and (3) two cases of anteriorly placed implants for degenerative disk disease/disk herniation.

When done posteriorly, the majority of cases were done with preservation of the spinous process and facet joints. In cases of severe spinal stenosis or spondylolisthesis, a complete facetectomy and spinous process resection was performed. These cases were treated with the implants and screw-plate fixation. When the facet joints were left intact, the spinous processes were wired using a Songer cable. The cable was applied with tension in order to create a dorsal tension band thereby locking the implants in a few degrees of lordosis. When inserted anteriorly, the implants were interconnected using a locking rod or a locking plate.

Patients were followed with a health survey, function questionnaire and pain questionnaire. These were obtained pre-operative, six weeks post-operative and one year post operative. X-rays were also taken at these intervals. Every case showed increase in disk height with no evidence of implant subsidence or migration. Segmental lordosis was maintained in every case except for one. In that one case, there was a slight loss of lordosis following reduction of a Grade II spondylolisthesis at L-3, L-4. Nineteen cases showed excellent results and one case showed a good result.

These results indicate that use of the oblate barbed implant of the present invention is very successful whether used in a posterior approach with instrumentation, in a posterior approach with preservation of the facet joints and usage of a Songer cable dorsal tension band or in an anterior approach with interlocking. The implant of the invention is easy to use, preserves and complements the normal anatomy, can be used in an interlocking embodiment and can be inserted either posteriorly or anteriorly using the same instrumentation and prosthetic supply.

While preferred embodiments of the invention have been described, the present invention is capable of variation and modification and therefore should not be limited to the precise details of the examples. The invention includes equivalents that fall within the purview of the following claims.

What is claimed is:

1. An intervertebral implant comprising:
   a. an elongated body having interconnected parallel side walls spaced apart;
   b. said walls each having two ends and a middle, and having upper and lower surfaces;
   c. said walls being shorter on each end than in the middle thereof; said upper and lower surfaces being provided with multiple barbs; and
   d. said barbs defined by front faces having a rearward tapered angle and connected substantially vertical rear faces; and
   e. a bone material inserted between said walls, said bone material provided within a bag member.

2. An intervertebral implant comprising:
   a. an elongated body having interconnected parallel side walls spaced apart;
   b. said walls each having two ends and a middle, and having upper and lower surfaces;
   c. said walls being shorter on each end than in the middle thereof; said upper and lower surfaces being provided with multiple barbs;
   d. said barbs defined by front faces having a rearward tapered angle and connected rear faces; and
   e. wherein said rear faces of said barbs are angled rearwardly relative to a direction of insertion of said intervertebral implant.

3. The intervertebral implant of claim 2, wherein said walls include openings therein.

4. The intervertebral implant of claim 2, wherein said body comprises titanium, titanium alloy or stainless steel.

5. The intervertebral implant of claim 4, wherein said body comprises titanium.

6. The intervertebral implant of claim 2, wherein a bone material is inserted between said walls.

7. The intervertebral implant of claim 6, wherein said bone material is provided within a bag member.

8. The intervertebral implant of claim 7, wherein said bag member is constructed of a polymer material.

9. The intervertebral implant of claim 7, wherein said bone material is comprised of a morphogenic protein.

10. An intervertebral implant system comprising:
    a. first and second elongated bodies each being narrower on each end than in the middle thereof;
    b. said bodies each having interconnected parallel walls;
    c. said parallel walls being shorter on each end than in the middle thereof, and having upper and lower surfaces, said surfaces being provided with multiple barbs;
    d. said barbs defined by front faces having a rearward tapered angle and connected rear;
    e. said rear faces of said barbs are angled rearwardly relative to the direction of insertion of said implant; and
    f. an interconnecter for connecting said first body to said second body.

11. The intervertebral implant of claim 10, wherein said interconnecter comprises:
    a. an elongated member having a channel along a portion of each end thereof;
    b. a slot positioned along an outer end of each of said bodies; said slot being sized to receive said elongated member therein; and
    c. a connecting device for securely attaching said elongated member to said outer end of each of said bodies.

12. The intervertebral implant of claim 11, wherein said connecting device is selected from the group consisting of: a rivet member, a press-fit pin and a threaded screw member.

13. The intervertebral implant of claim 10, wherein said first body and said second body each include openings therein and said interconnecter comprises an elongated member having an exterior shape; said elongated member being slidably and adjustably positioned within said openings that substantially correspond to the exterior shape of said elongate member.

14. The intervertebral implant of claim 13, wherein said elongate member is adjustably secured to said body with a securing member.

15. The intervertebral implant of claim 14, wherein said securing member comprises a threaded screw member.

16. An implant for locating intermediate joint structures comprising:

a. an elongated body having interconnected parallel side walls spaced apart;

b. said walls each having two ends and a middle, and having upper and lower surfaces;

c. said walls being shorter on each end than in the middle thereof; said upper and lower surfaces being provided with multiple barbs: and d. said barbs defined by front faces having a rearwardly tapered angle and connected substantially vertical rear faces; and e. a bone material inserted between said walls, said bone material provided within a bag member.

* * * * *

UNITED STATES PATENT AND TRADEMARK OFFICE
CERTIFICATE OF CORRECTION

PATENT NO.   : 6,325,827 B1  
DATED        : December 4, 2001  
INVENTOR(S)  : Paul S. Lin Page 1 of 1

It is certified that error appears in the above-identified patent and that said Letters Patent is hereby corrected as shown below:

<u>Column 8,</u>
Line 50, after the word rear, please insert -- faces --.

Signed and Sealed this

Fourteenth Day of May, 2002

*Attest:*

JAMES E. ROGAN
*Attesting Officer*   *Director of the United States Patent and Trademark Office*